United States Patent [19]

Halm et al.

[11] Patent Number: 5,281,739
[45] Date of Patent: Jan. 25, 1994

[54] PROCESS FOR MANUFACTURE OF ALKYLHALOSILANES

[75] Inventors: Roland L. Halm, Madison, Ind.; Charles S. Kuivila, La Grange; Regie H. Zapp, Carrollton, both of Ky.

[73] Assignee: Dow Corning Corporation, Midland, Mich.

[21] Appl. No.: 995,733

[22] Filed: Dec. 23, 1992

[51] Int. Cl.⁵ ................................. C07F 7/16
[52] U.S. Cl. .................................... 556/472
[58] Field of Search ......................... 556/472

[56] References Cited

U.S. PATENT DOCUMENTS

| | | | |
|---|---|---|---|
| Re. 33,452 | 11/1990 | Ward et al. | 556/472 |
| 2,380,995 | 8/1945 | Rochow | 556/472 |
| 2,380,996 | 8/1945 | Rochow | 556/472 |
| 2,466,412 | 4/1949 | Gilliam | 556/472 |
| 2,666,776 | 1/1954 | Nitzsche | 556/472 |
| 2,877,254 | 3/1959 | Enk et al. | 556/472 |
| 3,069,452 | 12/1962 | Rossmy | 556/472 |
| 3,536,743 | 10/1970 | Schrader et al. | 556/472 |
| 3,560,545 | 2/1971 | Schrader et al. | 556/472 |
| 4,218,387 | 8/1980 | Mass et al. | 556/472 |
| 4,281,149 | 7/1981 | Shade | 556/472 |
| 4,307,242 | 12/1981 | Shah et al. | 556/472 |
| 4,314,908 | 2/1982 | Downing et al. | 556/472 X |
| 4,864,044 | 9/1989 | Lewis et al. | 556/472 |
| 4,895,969 | 1/1990 | Feldner et al. | 556/472 |
| 4,973,725 | 11/1990 | Lewis et al. | 556/472 |
| 5,015,751 | 5/1991 | Feldner et al. | 556/472 |
| 5,059,343 | 10/1991 | Halm et al. | 556/472 X |

OTHER PUBLICATIONS

Clark, J.; Organometallic Chemistry 376:165–222 (1989).

Primary Examiner—Paul F. Shaver
Attorney, Agent, or Firm—William F. Boley

[57] ABSTRACT

The present invention is an improvement of the Direct Process for the manufacture of alkylhalosilanes by the contact of powdered metallurgical grade silicon with an alkyl halide in the presence of a copper catalyst. The improvement reduces lot-to-lot variations in silicon conversion to desired dialkyldihalosilanes. The improvement comprises alloying 0.01 to nine weight percent copper with the silicon to be used in the process and separating slag. In a preferred embodiment of the present process, silicon-copper alloy is pulverized to a powder and mixed with additional copper and other catalysts to form a contact mass reactive with alkylhalides.

29 Claims, No Drawings

PROCESS FOR MANUFACTURE OF ALKYLHALOSILANES

BACKGROUND OF INVENTION

The present invention is an improvement of the Direct Process for the manufacture of alkylhalosilanes by the contact of powdered metallurgical grade silicon with an alkyl halide in the presence of a copper catalyst. The improvement reduces lot-to-lot variations in silicon conversion to desired dialkyldihalosilanes. The improvement comprises alloying 0.01 to nine weight percent copper with the silicon to be used in the process and separating slag. In a preferred embodiment of the present process, the silicon-copper alloy is pulverized to a powder and mixed with additional copper and other catalysts to form a contact mass reactive with alkylhalides.

The Direct Process for producing alkylhalosilanes is well-known and has been refined and modified in many ways since Rochow first set forth the manner in which one could obtain alkylhalosilanes by contacting alkylhalides with silicon at elevated temperatures. The process is used for producing virtually all commercial alkylhalosilanes in the world today.

Rochow in U.S. Pat. No. 2,380,995, issued Aug. 7, 1945, taught passing a gaseous stream of methyl chloride into a heated tube where it contacted powdered silicon at about 300° C. Rochow obtained a mixture comprising 52 weight percent methyltrichlorosilane, 14.5 weight percent dimethyldichlorosilane, and lessor amounts of other silanes.

Commercially, the largest volume alkylhalosilane manufactured is dimethyldichlorosilane as this alkylhalosilane constitutes the backbone of most high volume commercial silicone products after it has been hydrolyzed and condensed to siloxane polymers. Therefore, it is to the benefit of the manufacturer to run the Direct Process to maximize the conversion of the raw materials to obtain the highest yield of dialkyldihalosilane. Thus one of the principal objectives of the instant invention is to control the Direct Process to maximize the overall yield of dialkyldihalosilanes, i.e. to cause the process to be as selective as possible in favor of dialkyldihalosilanes. A second objective of the instant invention is to maximize the overall yield from the raw materials. The more of the raw materials that are converted to silanes, the more economical is the process. A third objective of the present invention is to provide a copper catalyzed process where a portion of the catalytic copper can be provided by a low-cost copper source, for example, copper scrap. Copper used to create the silicon-copper alloy does not need to be in the powdered form, as is typically required for obtaining optimal performance of the Direct Process.

For purposes of this invention, the efficiency of converting raw materials is tracked by the amount of silicon charge that is converted to dialkyldihalosilane. When one considers that several million pounds of silanes are produced annually and consumed by the silicones commercial effort, it is obvious why small incremental increases in selectivity and raw materials conversion are important to the manufacturer of alkylhalosilanes.

Therefore, the manufacturers of silanes have set strict controls on the acceptable types and levels of impurities present in silicon used in the Direct Process. Clarke, *J. Organometallic Chemistry*, 376:165-222 (1989), provides a comprehensive review of the direct process for synthesis of methylchlorosilanes and the effects of impurities on the process. Despite the best efforts of silicon manufacturers to control the quality of silicon used in the direct process, considerable variation is observed in the performance of silicon provided by different silicon manufacturers and often between different lots of silicon provided by the same manufacturer. For unknown reasons some lots of silicon, which meet all of the silane manufacturer's quality criteria, still give lower conversion rates to the desired dialkyldihalosilanes.

Unexpectedly, the present inventors have found that this lot-to-lot variability in conversion to dialkyldihalosilanes experienced with metallurgical grade silicon can be reduced by alloying 0.01 to nine weight percent copper with the silicon to be used in the process and separating the slag. When this silicon-copper alloy is formed into a contact mass with an appropriate catalyst, the silicon which previously demonstrated reduced conversion to dialkyldihalosilanes performs comparable to good performing silicon.

Rochow, U.S. Pat. No. 2,380,995, issued Aug. 7, 1945, teaches that the reaction between silicon and a gaseous hydrocarbon halide is facilitated by the presence of a metallic catalyst such as copper. Furthermore, Rochow teaches that the copper may be alloyed with the silicon.

Rochow et al., U.S. Pat. No. 2.380.996, issued Aug. 7, 1945, teaches an improved method where a solid porous contact mass formed of powdered silicon and powdered copper is reacted with a hydrocarbon halide. This method, taught by Rochow, continues to be a method of choice for the commercial production of dialkyldihalosilanes, since use of the powdered materials provide for better control of the process than when a silicon-copper alloy is used.

Gilliam, U.S. Pat. No. 2,466,412, issued Apr. 5, 1949, teaches a process for preparing hydrocarbon substituted halosilanes where a hydrocarbon halide is reacted with an alloy of silicon and a metallic catalyst and the alloy is comminuted to a particular particle size of specific diameter and proportion by weight. Examples of metallic catalyst suggested by Gilliam are copper, nickel, tin, antimony, manganese, silver, and titanium.

Nitzsche, U.S. Pat. No. 2,666,776, issued Jan. 19, 1954, teaches the reaction of a hydrocarbon halide with an alloy which contains besides silicon and copper also a metal of the 5th to 8th groups of the periodic table, particularly cobalt, nickel, iron, or phosphorus. Nitzsche teaches that the alloy is preferably formed under slag or an inert gas. The finished alloy is reduced to pieces or ground into a powder and pressed into tablets. The alloy is then activated by wetting with a copper chloride solution or paste or by reacting with an acid such as hydrochloric acid.

Enk et al., U.S. Pat. No. 2,877,254, issued Mar. 10, 1959, reported that in the direct process, alloys of silicon with copper and heavy metals typically produced yields of 30 to 40 percent of the crude silane mixture as dimethyldichlorosilane. However, the yield of dimethyldichlorosilane could be improved to 60 to 70 percent if the aluminum content of the reaction mass was controlled below 0.2 weight percent. To reduce aluminum content, Enk et al. proposed treating the silicon, copper, heavy-metal alloy melt with a slag-forming substance such as a melt of magnesium silicate, or with magnesium or magnesium oxide in the presence of silicon dioxide.

Rossmy, U.S. Pat. No. 3,069,452, issued Dec. 18, 1962, teaches a use of a silicon-copper alloy as a catalyst for the reaction of powdered silicon with an alkylhalide. Rossmy teaches that the silicon-copper alloy catalyst is especially advantageous for use in a process where the catalyst and powdered silicon is sintered prior to reaction with the alkylhalide.

Despite the teachings of the cited prior art, variability in the performance of different lots of silicon in the Direct Process continues to plague the silicones industry. Surprisingly, the present inventors have found that if 0.01 to 9 weight percent copper is alloyed with silicon and slag appropriately removed, variability of performance of the silicon in the direct process is reduced. When the silicon-copper alloy is reacted with an alkylhalide in the presence of a catalytic concentration of copper, lot-to-lot variability in silicon conversion and in selectivity for dialkyldihalosilane is reduced.

SUMMARY OF INVENTION

The present invention is an improvement of the Direct Process for the manufacture of alkylhalosilanes by the contact of powdered metallurgical grade silicon with an alkyl halide in the presence of a copper catalyst. The improvement reduces lot-to-lot variations in silicon conversion to desired dialkyldihalosilanes. The improvement comprises alloying 0.01 to nine weight percent copper with the silicon to be used in the process and separating slag. In a preferred embodiment of the present process, silicon-copper alloy is pulverized to a powder and mixed with additional copper and other catalysts to form a contact mass reactive with alkylhalides.

DESCRIPTION OF INVENTION

The present invention is an improved process for the manufacture of alkylhalosilanes by the contacting of an alkylhalide with powdered metallurgical grade silicon in the presence of copper catalyst. The improvement comprises replacing the powdered metallurgical grade silicon with a powdered silicon-copper alloy comprising 0.01 to nine weight percent copper, the silicon-copper alloy formed by adding a copper source to the production of metallurgical grade silicon and separating the resulting silicon-copper alloy from slag.

The alkylhalosilanes which can be manufactured by the present invention are those having the general formula (I) $R_nSiX_{4-n}$ and (II) $R_nH_mSiX_{4-n-m}$ with the silanes of formula (I) being the preferred silanes of this invention. In the above formulae, each R is independently selected from a group consisting of alkyls comprising 1 to 4 carbon atoms, n has a value of 1, 2, or 3 in formula (I) and n has a value of 1 or 2 in formula (II), m has a value of 1 or 2, the sum of m+n cannot be greater than 3, and X is a halogen. The preferred silanes are those having the formula $R_2SiX_2$ where R is methyl or ethyl and X is chlorine. Most preferred is the silane $(CH_3)_2SiCl_2$, i.e. dimethyldichlorosilane.

The present process can be carried out as a batch or continuous process in standard reactors for reacting silicon with alkylhalides. The process can be conducted, for example, in a fluid-bed reactor or a stirred-bed reactor. Preferred is when the process is run as a continuous fluidized-bed operation.

The silicon-alloy useful in the present process is prepared by alloying metallurgical grade silicon with a source of copper to prepare an alloy comprising 0.01 to nine weight percent copper. The process of making the silicon copper alloy is another aspect of the present invention. By "metallurgical grade" silicon, it is meant a silicon comprising about 98 percent but less than 100 percent by weight silicon. Preferred is refined metallurgical grade silicon. More preferred is when the metallurgical grade silicon has been refined by an oxidative process. For example, the molten silicon can be refined by contacting with oxygen, air, or an oxidative compound such as $SiO_2$. In a preferred refining process, the molten silicon is contacted with oxygen or air in the presence of one or more slag forming components.

A source of copper is added to the molten metallurgical grade silicon to form an alloy comprising 0.01 to nine weight percent copper. When the metallurgical grade silicon is refined, the source of copper can be added to the molten metallurgical grade silicon before or after refining. Preferred is when the source of copper is added to the molten metallurgical grade silicon before refining. Preferred is when the silicon copper alloy comprises about 0.1 to four weight percent copper. A preferred copper source is copper metal. The copper source may be added to an electric-arc furnace during the carbothermic reduction of silicon dioxide to form molten silicon. The copper source may be added to the molten silicon after it is tapped from the furnace into a suitable ladle or other container.

Slag is separated from the silicon-copper alloy. The slag may be separated from the silicon-copper alloy while the alloy is in a molten or a solid state. Slag may be separated from molten silicon-copper alloy by, for example, filtering, tundish, raking, or skimming. Slag may be separated from solid silicon-copper alloy by, for example, crushing or grinding of the silicon and separating fines by screening or air sieving.

The inventors postulate that the reason for poor performance of some silicon in the direct process is the presence of low levels of nonmetallic impurities having densities similar to that of silicon. The addition of copper to the silicon changes the density of the copper-silicon alloy or otherwise enhances the separation of the nonmetallic impurities. The presence of copper during solidification of the copper-silicon alloy can also change the distribution and form of the impurities, both nonmetallic and intermetallic, throughout the solidified alloy making them less detrimental in the direct process.

It is preferred that the silicon-copper alloy be added to an appropriate reactor as a powder. The silicon-copper alloy powder can have average particle sizes ranging from greater than about 0.1 micron to 800 micron. The preferred average particle size is within a range of about 0.1 to 150 microns.

The present process requires the presence of copper as a catalyst within a range of about 0.1 to 10 weight percent of the silicon present in the process. The copper catalyst may be added to the process entirely as a component of the silicon-copper alloy. In a preferred embodiment of the present invention, a portion of the copper catalyst required in the process is provided by the silicon-copper alloy and the remainder is provided by copper metal, one or more copper compounds, or a mixture of copper metal and one or more copper compounds. More preferred is where the silicon-copper alloy provides about 0.1 to 4 weight percent of the copper required in the process as catalyst and the remainder of the copper required as catalyst is provided by a copper compound. A preferred copper compound is cuprous chloride.

The present process, in addition to copper, may employ other metals as catalysts. The scope of other metals contemplated as catalysts by the inventors are those metals known to those skilled in the art as promoters of the Direct Process. Examples of such catalytic metals are described by, and incorporated by reference herein, Halm, U.S. Pat. No. 4,602,101, issued Jul. 22, 1986; Halm, U.S. Pat. No. 4,946,978, issued Aug. 7. 1990; Halm, U.S. Pat. No. 4,762,940, issued Aug. 9. 1988; and Ward, U.S. Pat. No. Re. 33,452, reissued Nov. 20, 1990. These catalytic metals include, for example, phosphorus, phosphorous compounds, zinc, zinc compounds, tin, tin compounds, and mixtures thereof.

A preferred catalyst mixture for the present process comprises on an elemental basis by weight: 0.1 to 10 weight percent copper based on silicon present in the process, 100 to 10.000 ppm zinc, 5 to 200 ppm tin, and 25 to 2,500 ppm phosphorous.

When copper catalyst is added to the process in addition to that provided by the silicon-copper alloy or when other catalytic metals are added to the process it is preferred to form a heat activated contact mass prior to contact with the alkylhalide. The heat activated contact mass can be formed by forming a blend of silicon-copper alloy powder with powdered copper, copper compound, other catalytic metal, or a mixture thereof and heating the mixture to a temperature within a range of about 250° C. to 450° C. for up to 40 hours. The preferred temperature for activating the contact mass is within a range of about 270° C. to 350° C.

The silicon-copper alloy with or without additional catalysts is contacted with an alkylhalide. The alkyl substituent of the alkylhalide can comprise from one to four carbon atoms. The alkyl substituent can be, for example, methyl, ethyl, n-propyl, and isopropyl. The preferred halide is chlorine. The preferred alkylhalide is methyl chloride.

The present process can be conducted at a temperature within a range of about 250° C. to 350° C. The preferred temperature for conducting the present process is within a range of about 260° C. to 320° C. Even more preferred is a temperature within a range of about 280° C. to 320° C.

The following examples are provided to illustrate the present invention. These examples are not intended to limit the scope of the present claims.

EXAMPLE 1 (Not within the scope of the present claims)

A control baseline for the reaction of a good performing silicon with methyl chloride was established. A standard run consisted of forming a mixture comprising 100 parts of refined, ground, metallurgical grade silicon containing 0.16 weight percent (Wt %) aluminum, 0.004 Wt % calcium, and 0.32 Wt % iron; 6.5 parts of cuprous chloride; 600 ppm brass (containing 50 weight percent zinc); 36 ppm tin; and 2,000 ppm copper phosphide alloy. The process was conducted by charging the mixture to a reactor similar to that described by Mass et al., U.S. Pat. No. 4,218,387, issued Aug. 19, 1980. The temperature of the reactor was maintained at about 315° C. by means of a heated fluidized sand bath. The reactor was purged for 15 minutes with nitrogen gas. The nitrogen purge was then shut off and methyl chloride gas was fed to the reactor for a total of 44 hours during which time all products and unreacted methyl chloride were collected in a cold-trap maintained below minus 40° C. Weight loss of the reactor was used as an indicator of silicon conversion. The liquid collected in the cold-trap was analyzed by gas liquid chromotography (GLC) using a thermal conductivity (TC) detector. The "Performance" of the silicon in each run was calculated as the mass fraction of silicon consumed (i.e. mass Si consumed/mass Si charged) times the weight percent of dimethyldichlorosilane as a percent of the total weight of silane products formed. The average silicon Performance was determined to be 78.0 percent.

EXAMPLE 2

The effect of adding one weight percent copper as metal to a poor performing silicon was evaluated. The process was conducted similar to that described in Example 1. Duplicate control samples of the poor performing silicon were found to have a average Performance of 26.6 percent. The poor performing silicon contained 0.197 Wt % aluminum, 0.007 Wt % calcium, and 0.115 Wt % iron. A sample of the poor performing silicon was alloyed with one weight percent copper metal and the molten alloy carefully decanted from slag. Performance of duplicate samples of the copper-silicon alloy were tested under the same conditions as the control samples. The Performance of the duplicate samples of silicon-copper alloy were calculated as described in Example 1 as an average value of 56.3 percent.

EXAMPLE 3

The effect of adding two weight percent copper metal to a poor performing silicon was evaluated. The process was conducted similar to that described in Example 1. Duplicate control samples of the poor performing silicon were found to have a average Performance of 41.3 percent. The poor performing silicon contained 0.229 Wt % aluminum, 0.025 Wt % calcium, and 0.123 Wt % iron. A sample of the poor performing silicon was alloyed with two weight percent copper metal and the molten alloy was decanted from the slag. Performance of duplicate samples of the copper-silicon alloy were tested under the same conditions as the control samples. The performance of the duplicate samples of silicon-copper alloy were calculated as described in Example 1 as an average value of 73.0 percent.

We claim:

1. A process for the manufacture of alkylhalosilanes, the process comprising contacting a silicon-copper alloy, the alloy prepared by adding 0.01 to nine weight percent copper to molten metallurgical grade silicon and separating slag, with an alkylhalide, at a temperature within a range of about 250° C. to 350° C.

2. A process according to claim 1, where the metallurgical grade silicon is refined.

3. A process according to claim 1 further comprising mixing the silicon-copper alloy in a powdered form with a catalyst selected from a catalyst group consisting of copper, copper compounds, phosphorus, phosphorus compounds, zinc, zinc compounds, tin, tin compounds, and mixtures comprising two or more members of the catalyst group, to form a contact mass which is then contacted with the alkylhalide.

4. A process according to claim 3, where the metallurgical grade silicon is refined.

5. A process according to claim 4, where the metallurgical grade silicon is refined by an oxidative process.

6. A process according to claim 3, where the contact mass is heated prior to contact with the alkyl halide.

7. A process according to claim 3, where the contact mass comprises on an elemental basis by weight: 100 to 10,000 ppm zinc, 5 to 200 ppm tin, and 25 to 2,500 ppm phosphorous.

8. A process according to claim 1, where the copper is added to the process in the form of copper metal.

9. A process according to claim 1, where the silicon-copper alloy is formed by adding a source of copper selected from a group consisting of copper metal and copper compounds to an electric arc furnace during the carbothermic reduction of silicon dioxide to form molten silicon.

10. A process according to claim 1, where the silicon-copper alloy is formed by adding a source of copper selected from a group consisting of copper metal and copper compounds to molten silicon tapped from an electric arc furnace, the source of copper being added to the molten silicon prior to solidifying of the molten silicon.

11. A process according to claim 1, were the alkylhalide is methyl chloride.

12. In a process for the manufacture of alkylhalosilanes, the process including forming a contact mass comprising powdered metallurgical grade silicon and copper, a copper compound, or a blend of copper and a copper compound and contacting an alkylhalide with the contact mass at a temperature within a range of about 250° C. to 350° C.; the improvement comprising replacing the powdered metallurgical grade silicon with a powdered silicon-copper alloy comprising 0.01 to nine weight percent copper, the silicon-copper alloy formed by adding a copper source to molten metallurgical grade silicon and separating the resulting silicon-copper alloy from slag.

13. A process according to claim 12, where the metallurgical grade silicon is refined.

14. A process according to claim 13, where the metallurgical grade silicon is refined by an oxidative process.

15. A process according to claim 12, where the contact mass in heated prior to contact with the alkyl halide.

16. A process according to claim 12 further comprising a catalyst selected from a catalyst group consisting of phosphorous, phosphorous compounds, zinc, zinc compounds, tin, tin compounds, and mixtures comprising two or more members of the catalyst group.

17. A process according to claim 16, were the contact mass comprises on an elemental basis by weight: 100 to 10,000 ppm zinc, 5 to 200 ppm tin, 25 to 2,500 ppm phosphorous, and 0.1 to 9 weight percent copper.

18. A process according to claim 17, where the metallurgical grade silicon is oxygen refined and the contact mass is heated prior to contact with the alkyl halide.

19. A process according to claim 12, where the copper is added to the process in the form of copper metal.

20. A process according to claim 12, where the alkylhalide is methyl chloride.

21. A process for the manufacture of methylchlorosilanes, the process comprising heating a silicon-copper alloy, the alloy prepared by adding 0.1 to four weight percent copper to refined molten metallurgical grade silicon after the silicon is tapped from an electric arc furnace and before the silicon solidifies and removing slag from the silicon while the silicon is still in the molten state, with a catalyst comprising copper, zinc, tin, and phosphorous to form a contact mass and contacting the contact mass with methyl chloride at a temperature within a range of about 250° C. to 350° C.

22. A process according to claim 21, where the contact mass comprises on an elemental basis: copper within a range of greater than 0.1 weight percent to nine weight percent, 100 to 10,000 ppm zinc, five to 200 ppm tin, and 25 to 2,500 ppm phosphorous.

23. A process according to claim 22, where the catalyst comprises CuCl, zinc, tin, and a copper-phosphorous alloy.

24. In a process for the production of silicon for use in the manufacture of alkylhalosilanes by the reaction of metallurgical grade silicon with alkylhalide, the process including the carbothermic reduction of silicon dioxide in an electric-arc furnace, tapping molten silicon from the furnace, separating slag from the molten silicon and casting the molten silicon into ingots; the improvement comprising adding to the molten silicon after it is tapped from the furnace and prior to solidifying of the molten silicon, 0.01 to nine weight percent copper to form a silicon-copper alloy and separating the silicon copper alloy from slag.

25. A process according to claim 24, where the molten silicon is refined.

26. A process according to claim 25, where the molten silicon is refined by an oxidative process.

27. A process according to claim 25, where the silicon-copper alloy is separated from the slag prior to solidification of the silicon-copper alloy.

28. A process according to claim 25, where the silicon-copper alloy is separated from the slag after the silicon-copper alloy is solidified.

29. A process according to claim 1, where the copper is added to the molten metallurgical grade silicon.

* * * * *